Figure 1:
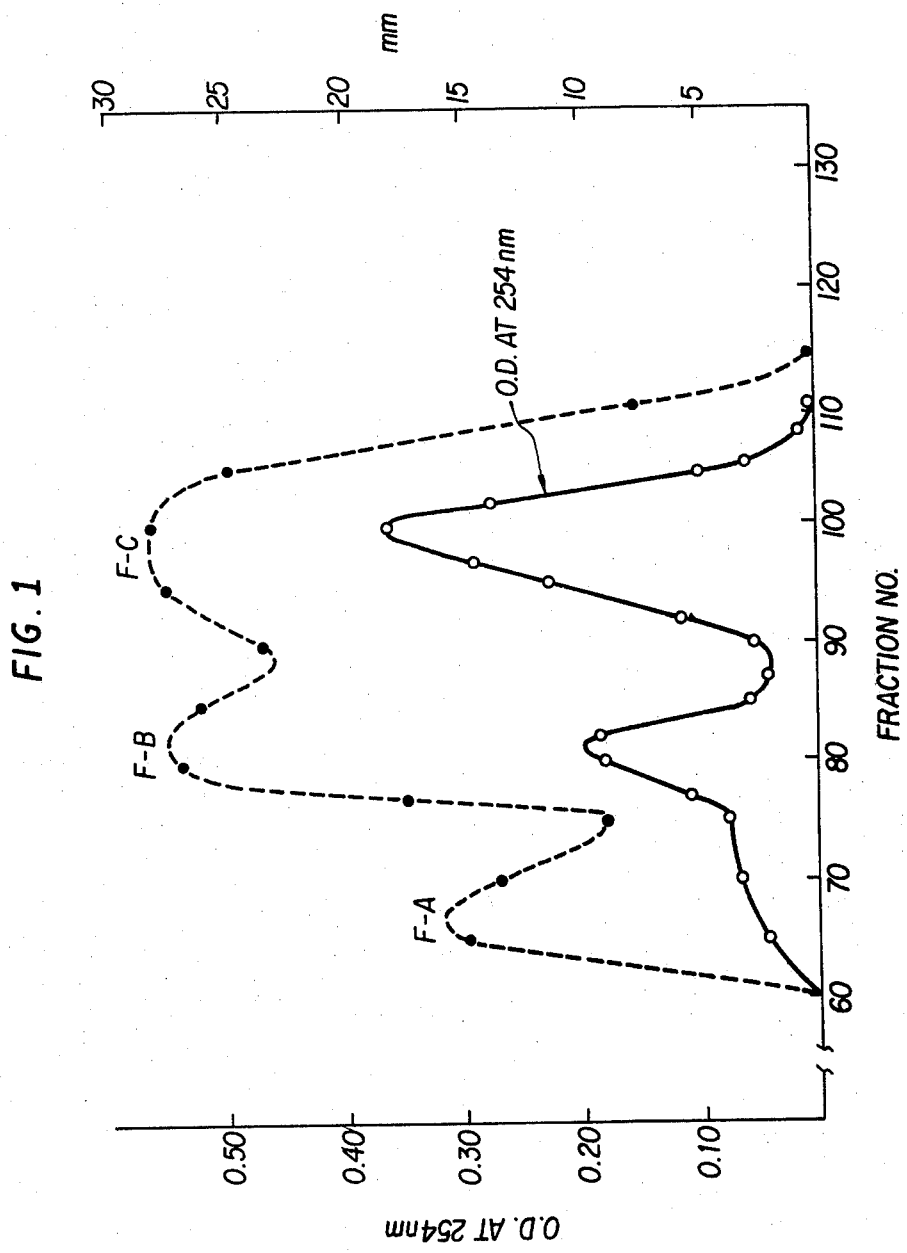

United States Patent [19]

Takahara et al.

[11] 4,294,754
[45] Oct. 13, 1981

[54] RING PEPTIDE ANTIBIOTICS, PERMETIN A AND A PROCESS FOR PRODUCING THE SAME

[75] Inventors: Yoshiyuki Takahara, Tokyo; Yoshiteru Hirose, Kamakura; Yoko Takeuchi; Asao Murai, both of Tokyo; Masatsune Kainosho, Kawasaki; Sawao Murao, Sakai, all of Japan

[73] Assignee: Ajinomoto Company, Incorporated, Tokyo, Japan

[21] Appl. No.: 27,029

[22] Filed: Apr. 4, 1979

[30] Foreign Application Priority Data

Apr. 7, 1978 [JP] Japan .................. 53-40999

[51] Int. Cl.³ .................. C07C 103/52; C12P 21/04
[52] U.S. Cl. .................. 260/112.5 R; 435/71
[58] Field of Search .................. 260/112.5 R

[56] References Cited
PUBLICATIONS

Kato et al., Chem. Abstr. 87, 1977 53565r.
Taylor et al., Chem. Abstr. 85, 1976 76306e.
Matsuura et al., Chem. Abstr. 85, 1976 3871a.
Yasui; Chem. Abstr. 85, 1976 31609q.
Arai et al., Chem. Abstr. 85, 1976 31611j and 76349w.
Shoji et al., Chem. Abstr. 85, 1976 61361v.
Sogn; Journal of Medicinal Chemistry, 1976, vol. 19, No. 10, pp. 1228–1231.

*Primary Examiner*—Delbert R. Phillips
*Attorney, Agent, or Firm*—Oblon, Fisher, Spivak, McClelland & Maier

[57] ABSTRACT

A purified ring peptide antibiotic of the following empirical formula:

Nα-(3-hydroxy-4-methyl-1-oxohexyl)-L-α,γ-diaminobutyryl-L-isoleucyl-L-α,γ-diaminobutyryl-D-phenylalanyl-L-leucyl-L-α,γ-diaminobutyryl-D-valyl-L-leucyl-L-serine (9-1)-lactone and which has the following structural formula:

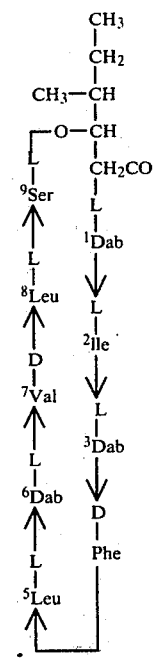

and wherein Dab represents 2,4-diamino butyric acid.

1 Claim, 3 Drawing Figures

RING PEPTIDE ANTIBIOTICS, PERMETIN A AND A PROCESS FOR PRODUCING THE SAME

BACKGROUND OF THE INVENTION

Field of the Invention

This invention relates to the ring peptide antibiotics, Permetin A.

SUMMARY OF THE INVENTION

After an eager investigation to find new and more useful antibiotics, the new ring peptide antibiotics, Permetin A, which has high and broad anti-microbial activity to gram-positive bacteria gram-negative bacteria and fungi, has been found in the culture liquid of Bacillus.

Permetin A is:

N$\alpha$-(3-hydroxy-4-methyl-1-oxohexyl)-L-$\alpha$,$\gamma$-diaminobutyryl-L-isoleucyl-L-$\alpha$,$\gamma$-diaminobutyryl-D-phenylalanyl-L-leucyl-L-$\alpha$,$\gamma$-diaminobutyryl-D-valyl-L-leucyl-L-serine (9-1)-lactone; and has the following structural formula:

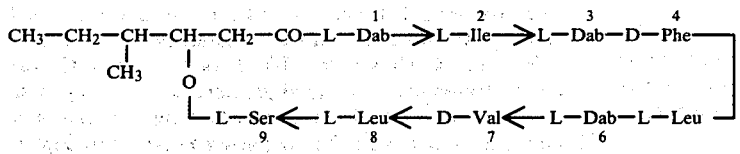

(In the formula, Dab represents 2,4-diamino-butyric acid).

Various ring peptide antibiotics produced by bacteria are known. The known ring peptide antibiotics, Polymixins, Colistins, Circutins and Polypeptin contain 2,4-diamino-butyric acid in their molecule as in Permetin A. However Permetin A is different from the known peptide antibiotics in the point that the known antibiotics contain threonine in their molecules.

The antibiotics EM-49 (Japanese Published Unexamined Patent Application No. 4688/1973) and AB-2 (Published Examined Patent Application No. 2958/1978) contain 2,4-diamino-butyric acid and do not contain threonine, however, EM-49 is different from Permetin A since EM-49 does not contain valine, serine and isoleucine.

Although AB-2, which has been found by some of the present inventors, contains 2,4-diamino-butyric acid, leucine, isoleucine, phenylalanine, valine and serine in the ratio of 6:2:1:1:1:1, the ratio of the amino acids in Permetin A is 3:2:1:1:1:1. When Permetin A and AB-2 are compared in their anti-microbial activities, minimum inhibitory concentrations (MIC) of AB-2 to *Pseudomonas aeruginosa* ATCC 10145 and *Salmonella typhimurium* AJ 3224 are 125 mcq/ml and 62.5 mcq/ml, respectively, and those of Permetin A are 12.5 mcq/ml and 25 mcq/ml, respectively. Permetin A is thus higher than AB-2 in its anti-microbial activity.

Permetin A has high anti-microbial activities to such wide range of microorganisms as gram-positive bacteria, gram-negative bacteria and fungi. The minimum inhibitory concentrations of Permetin A to typical microorganisms are shown in Table 1.

TABLE 1

Minimum Inhibitory Concentration (MIC) of Permetin A

| Tested Microorganisms | MIC mcq/ml | Medium |
|---|---|---|
| *Escherichia coli* NIH JC-2 | 12,5 | A |
| *Escherichia coli* 61 | 12,5 | " |
| *Escherichia coli* 1236 | 12,5 | " |
| *Salmonella typhimurium* AJ 3224 | 12,5 | " |
| *Klebsiella preumoniae* GN 69 | 25 | " |
| *Klebsiella preumoniae* GM 118 | 12,5 | " |
| *Klebsiella preumoniae* 29 | 12,5 | " |
| *Klebsiella preumoniae* 48 | 12,5 | " |
| *Klebsiella preumoniae* 37 | 12,5 | " |
| *Pseudomonas aeruqinosa* ATCC 10145 | 25 | " |
| *Pseudomonas aeruqinosa* IFO 3445 | 12,5 | " |
| *Pseudomonas aeruqinosa* 4424 | 25 | " |
| *Pseudomonas aeruqinosa* 4049 | 25 | " |
| *Serratia marcescens* 32 | 12,5 | " |
| *Serratia marcescens* 34 | 12,5 | " |
| *Enterobacter cloacae* 33 | 12,5 | " |
| *Enterobacter cloacae* 35 | 12,5 | " |
| *Proteus vulgaris* GN 76/C 1 | >50 | " |
| *Proteus vulgaris* 2 | >50 | " |
| *Proteus vulgaris* 5 | >50 | " |
| *Proteus milabiles* 1 | 12,5 | " |
| *Proteus milabiles* 3 | >50 | " |
| *Proteus milabiles* 4 | >50 | " |
| *Staphirococcus aureus* 209P | 6,25 | " |
| *Staphirococcus aureus* 14 | 6,25 | " |
| *Bacillus subtilis* AJ 1234 | 3,13 | " |
| *Bacillus sereus* AJ 1310 | 12,5 | " |
| *Brevibacterium* AJ 1511 | 6,25 | " |
| *Clostridium sp* ZSB-5 | 6,25 | B |
| *Clostridium sp* ZSB-13 | 25 | " |
| *Clostridium sp* ZSB-14 | 25 | " |

(Medium A: Heart infusion medium, Medium B: TEP medium).

The anti-microbial activity test of Table 1 was carried out using a typing apparatus. In this case, each microorganism tabulated in Table 1 was inoculated on the agar plate medium containing Permetin A, and cultured at 30° C. for 24 hours under aerobic or unaerobic (the steel wool method) conditions.

The Permetin A of the invention is produced by culturing a microorganism capable of producing Permetin A in a nutrient culture medium under aerobic conditions. The microorganisms applicable to the invention include *Bacillus circulans* AJ 3902 (FERM-P 3097, IFO 13894).

The culture medium is conventional, and contains an assimilable carbon source, an assimilable nitrogen source and inorganic salts. The assimilable carbon sources include saccharides, such as glucose and sucrose, the assimilable nitrogen sources include peptone, meat extract, yeast extract, ammonium sulfate, ammonium nitrate and urea, and the inorganic salts include sodium chloride, phosphates, sulfates, potassium salts, sodium salts, magnesium salts and ferrous salts.

The cultivation of the microorganisms is carried out at 25° to 45° C. for 24 to 72 hours under aerobic conditions. The aeration is carried out by shaking or by aerating with stirring.

After the cultivation, most of Permetin A is extracellularly accumulated in the culture broth. Permetin A is recovered from the culture broth by extraction using various organic solvents such as n-butanol, by precipitation using sodium Helianthate, by ion-exchange chromatography using various ion-exchangers such as CM-cellulose, and by gel filtration method, etc.

For example, the culture broth is first centrifuged, and Permetin A is extracted with n-butanol from the supernatant. The n-Butanol layer is collected, and then n-butanol is evaporated. The residue is dissolved in water, and sodium Helianthate is added to the aqueous solution. The precipitate so produced is filtered, and the residue is added to an aqueous acid solution. The insoluble materials are removed by centrifuging. The supernatant is treated by the gel filtration method using Sephadex G-25, and anti-microbially active fractions of the eluate are collected. Subsequently, the collected fractions are passed through the CM-cellulose column, and the active compounds are eluted with sodium chloride solution while sodium chloride concentration of the eluting agent is elevated. Active fractions of the eluate separate into three parts. The last active part is collected, and purified by the gel filtration method using Sephadex LH-20. When the above treatments using CM-cellulose and Sephadex LH-20 are repeated once more, pure Permetin A can obtained.

Having generally described this invention, a further understanding can be obtained by reference to certain specific examples which are provided herein for purposes of illustration only and are not intended to be limiting unless otherwise specified.

EXAMPLE 1

100 ml of an aqueous culture medium of which pH was 6.0, containing 3 g peptone, 1 g meat extract, and 0.3 g NaCl was put into a 500 ml shake flask and heated at 120° C. for 20 minutes.

*Bacillus circulans* FERM-P 3097 IFO 13894 grown on Boullion agar slant at pH 6.0 and 30° for 24 hours was inoculated in the sterilized culture medium and cultured at 30° C. for 3 days with shaking (120 Oscill./min., 7.0 cm in width). The cultured broth thus obtained was centrifugated to remove the microbial cells, and the supernatant solution was concentrated under reduced pressure to obtain 20 ml of concentrated solution. The concentrated solution, was poured into a separatory funnel together with 150 ml of n-butanol, and Permetin A was extracted in the funnel by shaking. Then the n-butanol layer containing Permetin A was separated from the aqueous solution and concentrated under reduced pressure to precipitate Permetin A. Permetin A was then, separated from the concentrated solution by centrifugation, dissolved into 100 ml of water and centrifugated (10,000 rpm) to remove insoluble impurities. 5.0 g sodium Helianthate dissolved into a mixture solution of 25 ml dimethylformamide and 75 ml water was added to the supernatant solution containing Permetin A to precipitate Permetin A. Permetin A thereby precipitated was separated from the mother liquor by centrifugation and then dissolved into 90 ml dimethylformamide. The solution was centrifugated to remove insoluble impurities and 1.5 liters of water were added to the supernatant solution from which Permetin A was re-precipitated. The precipitate was separated from the mother liquid by centrifugation and then dissolved into 50 ml of 0.36 N HCl. Helianthic acid, was thereby precipitated and was removed from the acidic solution by filtration.

Permetin A in the acidic solution was then extracted by 100 ml butanol in the same manner described above and dried up under reduced pressure.

The Permetin A preparation thus obtained was dissolved into an aliquot of 0.02 N HCl, and was gel filtrated using a column of Sephadex G-25 (1.5×90 Cm, a molecular sieve, material manufactured by Pharmacia Fine chemicals) equilibrated with 0.02 N HCl and fractions containing Permetin A were collected.

The fractions containing Permetin A were concentrated and re-gel filtrated using the same column. The fractions containing Permetin A were collected, concentrated, and dried up under reduced pressure to obtain 2.0 g partialy purified Permetin A preparation in the form of white powder. 1.0 g of Permetin A preparation was dissolved into an aliquot of mixture solution (0.05 M ammonium formate buffer solution (ph 7.0): methanol=1:1) and was adsorbed on the top a CM-cellulose column (2.5×40 cm) buffered with the same mixture solution. Then Permetin A adsorbed was eluted by linear gradient elution of NaCl (0 to 1.0 M).

FIG. 1 shows an ion-exchange chromatogram obtained. Numbers on the abscissa indicate the fraction numbers (1 Fraction=5.0 ml) and the vertical axis indicate the optical density at 254 nm and anti-microbial activity (shown as a diameter of halo) of each fraction.

Fraction C shown in FIG. 1 as fraction F-C was concentrated under reduced pressure and dried up. The Permetin A preparation was dissolved into an aliquot of methanol and was gel filtrated using a column of Sephadex LH-20 (2.5×40 cm, a molecular sieve material, manufactured by Pharmacia Fine Chemicals) buffered with methanol to remove inorganic salts.

Permetin A contained in the eluted fraction was further purified by both CM-cellulose ion-exchanging chromatography and Sephadex LH-20 gel filtration in the same manner as described above and 550 mg of purified Permetin A in the form of white powder was obtained.

Amino acid contents in the white powder thus obtained are shown in Table 2.

TABLE 2

| Amino Acid Contents | | |
|---|---|---|
| Constituent Amino Acids | Contents (%) | Molar ratio (as phe = 1) |
| 2,4-Dab | 38,3 | 3,0 |
| Ser | 5,4 | 0,91 |
| Val | 7,4 | 1,01 |
| Ile | 7,9 | 0,95 |
| Lev | 7,4 | 2,08 |
| Phe | 10,5 | 1,00 |

(The contents were determined after heating the white powder in 6 N HCl at 110° C. for 72 hours). When the white powder was heated at 110° C. for one hour in 6 N HCl, and diazotized, an organic acid was found by gas-chromatography. The organic acid was determined by mass-spectrum and NMR-spectrum as 3-hydroxy-4-methyl-hexanoic acid having the following formula:

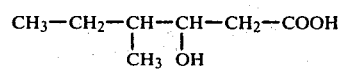

Figure 2:
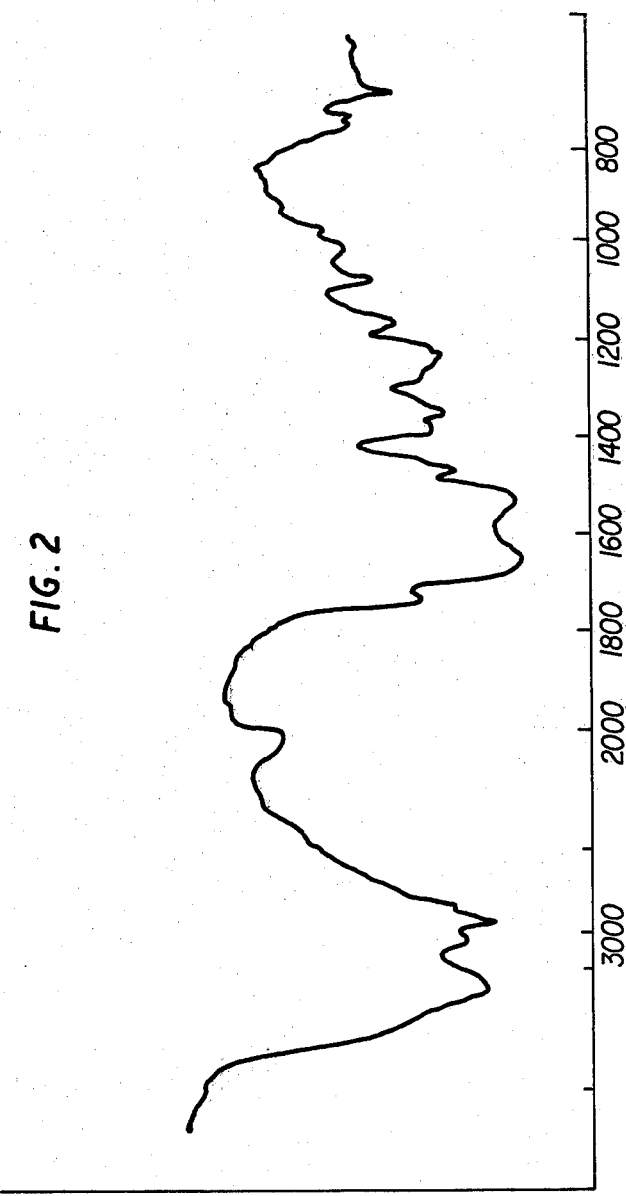
Figure 3:
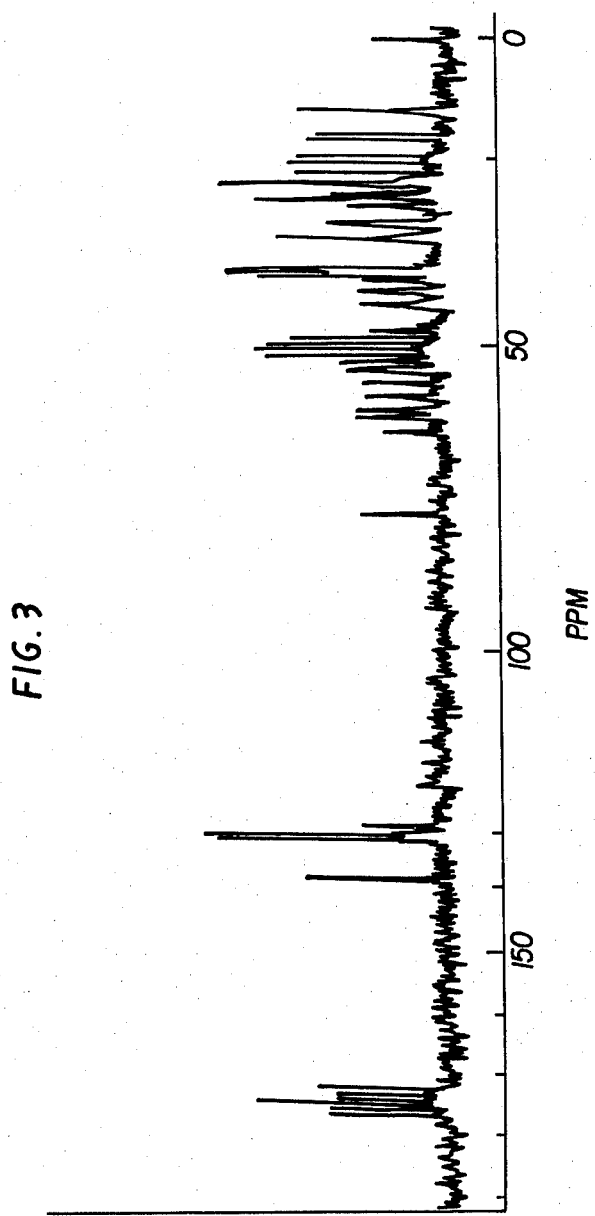

IR-spectrum of the white powder are shown in FIG. 2 and FIG. 3, respectively.

Having now fully described this invention, it will be apparent to one of ordinary skilled in the art that many changes and modifications can be made thereto without departing from the spirit or the scope of the invention said forth herein.

What is claimed as new and intended to be covered by Letters Patent is:

1. A purified ring peptide antibiotic having the following empirical formula:

Nα-(3-hydroxy-4-methyl-1-oxohexyl)-L-α, γ-diaminobutyrl-L-isoeucyl-L-α,γ-diaminobutryl-D-phenylalanyl-L-leucyl-L-α,γ-diaminobutyrl-D-valyl-L-leucyl-L-serine(9-1)-lactone;

and which has the following structural formula:

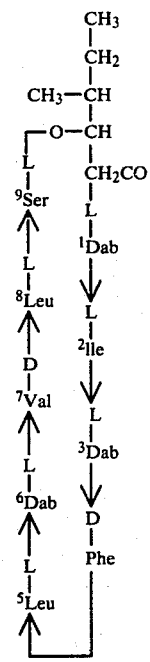

and wherein Dab represents 2,4-diamino butyric acid.

* * * * *